United States Patent [19]

Matwijcow

[11] Patent Number: 5,207,696
[45] Date of Patent: May 4, 1993

[54] SURGICAL SCALPEL

[75] Inventor: Robert J. Matwijcow, Salem, N.Y.

[73] Assignee: Medical Sterile Products, Inc., Rincon, P.R.

[21] Appl. No.: 876,266

[22] Filed: Apr. 30, 1992

[51] Int. Cl.⁵ .................... A61B 17/32; B26B 5/00
[52] U.S. Cl. .................... 606/167; 30/151; 30/335
[58] Field of Search .......... 606/166, 167, 172, 181, 606/182, 185; 30/151, 162, 164, 167, 286, 220, 335; 128/751

[56] References Cited

U.S. PATENT DOCUMENTS

| | | | |
|---|---|---|---|
| 2,380,787 | 7/1945 | Pierce et al. | 30/220 |
| 2,735,176 | 2/1956 | Costin . | |
| 3,905,101 | 9/1975 | Shepherd . | |
| 3,906,626 | 9/1975 | Riuli | 30/335 |
| 3,945,117 | 3/1976 | Beaver | 606/172 |
| 4,491,132 | 1/1985 | Aikins | 606/167 |
| 4,569,133 | 2/1986 | Schmidt | 606/172 |
| 4,576,164 | 3/1986 | Richeson | 606/167 |
| 4,713,885 | 12/1987 | Keklak et al. | 30/335 |
| 4,735,202 | 4/1988 | Williams . | |
| 4,757,612 | 7/1988 | Peyrot | 30/151 |
| 5,071,426 | 12/1991 | Dolgin et al. . | |

FOREIGN PATENT DOCUMENTS

| | | | |
|---|---|---|---|
| 3722899 | 1/1989 | Fed. Rep. of Germany | 606/167 |
| 9011725 | 10/1990 | World Int. Prop. O. | 606/167 |

Primary Examiner—C. Fred Rosenbaum
Assistant Examiner—William W. Lewis

[57] ABSTRACT

A scalpel includes a blade carrier and blade shield equally movable but in opposite longitudinal directions in response to longitudinal movement of an actuator along the upper edge of the scalpel housing. Equal and opposite motion is achieved using a pinion disposed in the housing and engaged on opposite diametric sides by racks secured to the blade shield and blade carrier. The actuator is compressible to remove stop members secured thereto from respective recesses, thereby permitting movement of the blade carrier and blade shield from defined extreme positions.

13 Claims, 2 Drawing Sheets

SURGICAL SCALPEL

BACKGROUND OF THE INVENTION

1. Technical Field

The present invention pertains to surgical scalpels and, more particularly, to a surgical scalpel having a movable protective shield.

2. Discussion of the Prior Art

Surgical scalpels are sometimes provided with a blade shield or guard to protect against accidental cutting of operating room personnel during handling of the scalpel. Such protection has become critically important in recent years in view of the epidemic nature of the AIDS virus being spread by intermixing very small amounts of blood. It is important, however, that the blade guard or shield be selectively movable by the surgeon to expose the blade for cutting without causing unnecessary or uncomfortable hand movement by the surgeon, and without unduly complicating or enlarging the scalpel structure. In this regard, a surgeon typically holds a scalpel between the thumb and the facing side of the middle finger with the forefinger disposed along the top surface of the scalpel. Since the forefinger is typically the most precisely controlled finger on one's hand, it is desirable to provide a blade shield that can be moved into and out of extended position by a simple movement of the surgeon's forefinger without requiring movement of the thumb or middle finger, and without requiring repositioning of the unit in the surgeon's hand. It is also desirable that the scalpel be capable of being manufactured at sufficiently low cost to be disposable after a single use, thereby eliminating the need to sterilize the scalpel after each surgical procedure.

The prior art discloses a variety of surgical scalpel structures that reflect attempts to address the above-described considerations. For example, U.S. Pat. No. 2,735,176 (Costin) discloses a surgical knife having a hollow handle serving as a sheath for a blade disposed for slidable extension and retraction between cutting and shielded positions. Movement of the blade requires the surgeon to at least rearrange the handle in his/her hand and, in most cases, requires two-handed actuation. Further, sheath-type scalpels generally require complex locking and retraction mechanisms, resulting in a cost that is significantly higher than is practical for disposability. The scalpels disclosed in U.S. Pat. Nos. 3,905,101 (Shepard) and 3,906,626 (Riuli) have sheaths in which a handle carrying the blade is slidable between protective and cutting positions, but require two hands to effect the sliding motion.

The scalpel disclosed in U.S. Pat. No. 5,071,426 (Dolgin et al) includes a blade guard having an actuating mechanism that is automatically contacted by the surgeon's thumb and forefinger when these fingers are placed along opposite sides of the scalpel handle. This finger position is described in the Dolgin et al patent as being the normal position in use of the scalpel, even though many surgeons generally prefer the position described above wherein the thumb and the facing side of the middle finger are disposed on opposite sides of the handle, and the forefinger is disposed along the top edge of the handle. Nevertheless, the Dolgin et al guard actuation mechanism is a somewhat complex structure comprising an actuating arm extending at an acute angle from the rear end of the handle and terminating in a linkage assembly extending entirely across the handle to project transversely from the opposite side of the unit. In one embodiment the linkage includes a first rack movable transversely when the actuator is squeezed in order to rotate a first pinion mounted inside the handle on a common axle with a second pinion. The second pinion drives a second rack disposed on the blade guard to move the blade guard longitudinally in response to transverse actuator movement. The ratio of teeth on the respective pinions provides a mechanical advantage permitting the second rack to move a greater distance than the actuator rack. The transverse projecting actuator and linkages make the unit somewhat cumbersome and unwieldy as well as difficult to store efficiently. Moreover, the transversely projecting linkage is subject to being misaligned during storage or mishandling, resulting in the failure of the actuating mechanism. Further, the complexity of the overall actuating mechanism itself renders the mechanism susceptible to failure.

The surgical scalpel of the present invention obviates the above-described problems of the prior art by providing a disposable scalpel having a blade shield capable of selective extension and retraction without movement of the surgeon's hand from the preferred cutting position and without requiring a complex and inconvenient structure.

OBJECTS AND SUMMARY OF THE INVENTION

It is therefore an object of the present invention to provide a disposable surgical scalpel having the desirable features described above without the disadvantages present in prior art scalpels.

It is another object of the present invention to provide a disposable surgical scalpel having a thin profile and a selectively actuable blade shield that can be moved by the forefinger of the surgeon while holding the scalpel between his/her thumb and middle finger.

A further object of the invention is to provide a method and apparatus for moving a blade shield in a surgical scalpel without requiring reorientation of the scalpel in the surgeon's hand from the desired cutting position, and without requiring transverse projections from the scalpel body, while providing a mechanical advantage such that relative movement between the blade and shield is greater than the movement of the surgeon's actuating finger.

In accordance with the present invention, a disposable surgical scalpel includes an elongated handle and a cover defining a housing wherein a blade carrier and a blade shield are disposed for longitudinal movement relative to each other and to the housing. A pinion is disposed in the housing for rotation about a stationary pivot pin extending transversely across the housing. The blade carrier and blade shield include respective racks engaging diametrically opposite sides of the pinion such that rotation of the pinion in either direction results in longitudinal movement of both the shield and carrier in opposite directions. An actuator secured to either the blade carrier or the blade shield is accessible along the top edge of the housing to be displaced longitudinally of the housing by the surgeon's forefinger. In the preferred embodiment the actuator is part of the blade carrier structure such that longitudinal displacement of the actuator causes the carrier rack to rotate the pinion and thereby cause the blade shield to be displaced longitudinally in the opposite direction. Relative longitudinal movement between the blade carrier and blade shield is twice the longitudinal movement of the surgeon's forefinger by virtue of the fact that the shield and carrier are moved the same distance in opposite directions.

The above and still further objects, features and advantages of the present invention will become apparent upon consideration of the detailed description set forth below, particularly when taken in conjunction with the accompanying drawings wherein like reference numerals in the various figures are utilized to describe like components.

BRIEF DESCRIPTION OF THE DRAWINGS

FIG. 6 is a detailed side view in elevation of a portion of the blade carrier and handle in the surgical scalpel of FIG. 1 shown in the extended position of the blade.

FIG. 7 is a detailed side view in elevation of a portion of the blade carrier and handle of the surgical scalpel of FIG. 1 shown in the retracted position of the blade.

DESCRIPTION OF THE PREFERRED EMBODIMENTS

Figure 1:
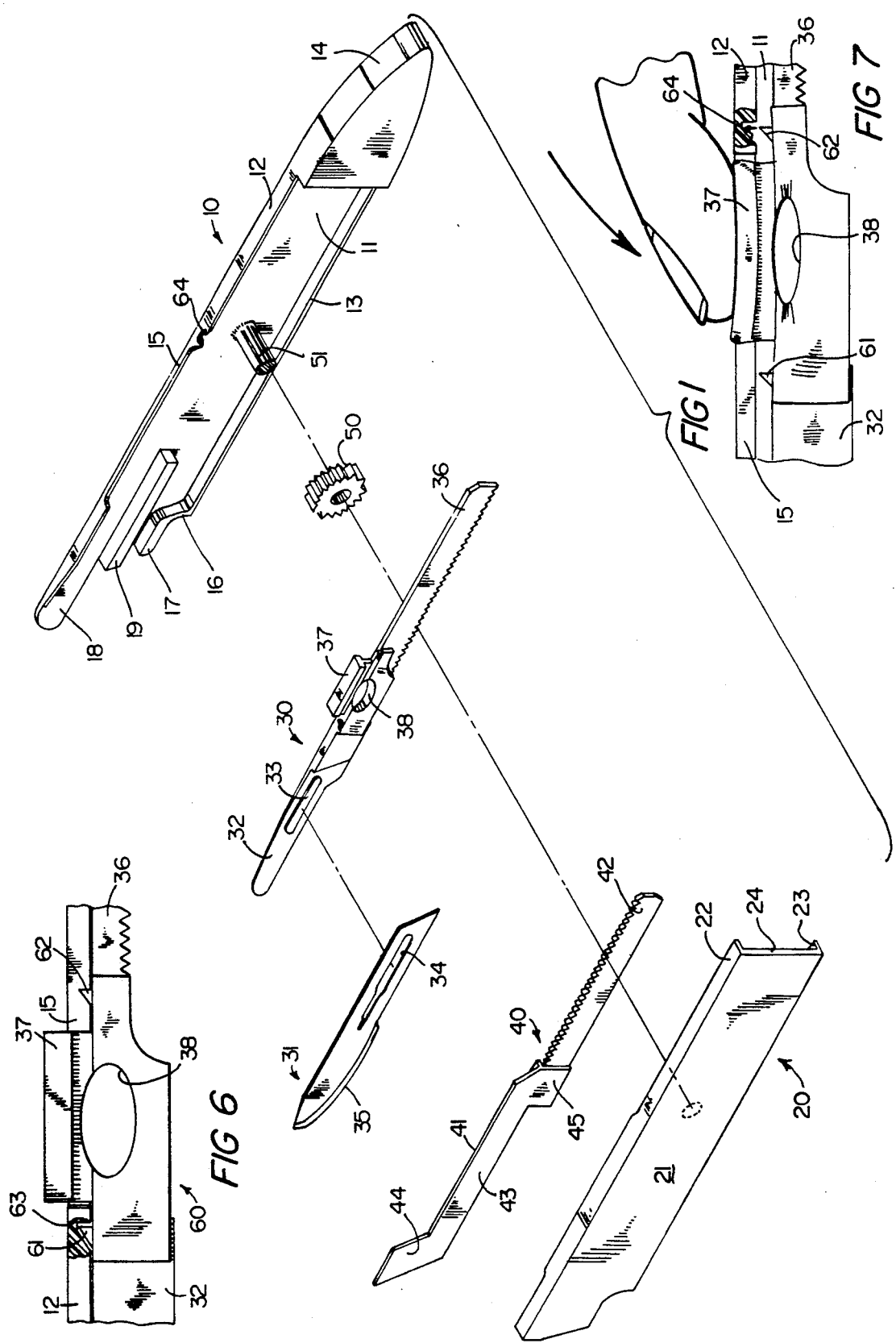
FIG. 1 is an exploded view in perspective of a preferred embodiment of the surgical scalpel of the present invention.

Referring to the drawings in greater detail, a surgical scalpel constructed according to the present invention includes a handle 10 and a cover 20 defining an elongated housing. Disposed within the housing are a blade carrier 30 and a blade shield 40, each being movable longitudinally of the housing. A pinion 50 is also disposed within the housing and is rotatable about an axis extending transversely of the longitudinal housing dimension. A scalpel cutting blade 31 is secured to blade carrier 30 and is movable therewith.

Handle 10 is an elongated member having a sidewall 11 with a length greater than its height, a top wall 12 and a bottom wall 13. The side of handle 10 opposite sidewall 11 is open along most of its length except for the rearward or butt end 14 of the handle. The rearward or butt end 14 is formed between converging or tapered portions of top and bottom walls 12 and 13 with a contour that comfortably fits against the heel of the surgeon's palm. The transverse dimension of butt end 14 also tapers rearwardly from a location of maximum width (i.e., the transverse dimension) of handle 10. Butt end 14 is preferably solid and typically occupies the rearward twenty to twenty-five percent of the handle length.

Immediately forward of butt end 14, top and bottom walls 12 and 13, respectively, have transverse dimensions that are approximately half the maximum width of the handle. At a location somewhat forward of butt end 14, the top wall is entirely cut-away or interrupted to define a slot 15 extending longitudinally a predetermined distance along the handle. Slot 15 typically has a length between twenty-five and thirty percent of the handle length and is spaced from the forward portion of butt end 14 by a distance between thirty and thirty-five percent of the handle length. Top wall 12 resumes forwardly of slot 15 and tapers in width at the distal end of the handle.

Bottom wall 13 includes a long straight section extending parallel to top wall 12 from the forward portion of butt end 14 to a location just below the forward end of slot 15. At that location bottom wall 13 angles sharply at 16 toward top wall 12 and then bends into a straight section 17 extending a short distance forwardly where it terminates considerably short of the forward termination of top wall 12. Typically, angled section 16 is disposed at a location spaced from the distal end of the handle by a distance that is approximately twenty percent of the handle length; straight section 17 has a length typically on the order of five percent of the handle length. Forwardly of straight section 17, bottom wall 13 is absent, and sidewall 11 is cut away to provide a distally projecting finger-like member 18 at the forward end of the handle.

A journal pin 51 has one end secured to or integrally formed with the interior surface of handle sidewall 11. Pin 51 extends transversely of the handle to a length beyond the widths of top wall 12 and bottom wall 13 and corresponding to the maximum width of the handle. Also formed with or secured to the interior surface of sidewall 11 is a longitudinally extending separator 19 serving to separate the space along the interior surface of sidewall 11 into two longitudinally extending guide channels. Separator 19 extends longitudinally from a location below approximately the midpoint of slot 15 to a location slightly beyond the forward end of distal section 17 of bottom wall 13. One of the guide channels is defined between separator 19 and bottom wall 13; the other guide channel is defined between separator 19 and top wall 12.

Cover 20 includes a sidewall 21, a top wall 22 and a bottom wall 23. The exposed longitudinal edges of top wall 22 and bottom wall 23 are adapted to abut and be secured to corresponding edges of top wall 12 and bottom wall 13, respectively, of handle 10. The widths of the top and bottom walls of the handle and cover thus define the maximum transverse dimension of the housing, whereas the space between cover sidewall 21 and handle sidewall 11 constitutes the housing interior. The rearward edge 24 of sidewall 21 is arranged to abut and be secured to the forward facing surface of butt end 14 in a manner such that the transition between butt end 14 and cover 20 is smooth and free from discontinuities. Securing of the various edges of cover 20 to handle 10 may be effected by appropriate adhesive, ultrasonic welding, or any suitable means. The forward end of sidewall 21 is contoured to substantially match and follow the contour of angled section 16 and straight section 17 of handle bottom wall 13, and then terminates to permit the finger-like projection 18 of handle 10 to extend uncovered from the front of the unit.

Blade carrier 30 is a thin elongated member disposed adjacent the interior surface of handle sidewall 11 in the scalpel housing. A forward or distal end section 32 of blade carrier 30 is substantially planar and is positioned to extend longitudinally in the guide channel defined between separator 19 and handle top wall 12. On the surface of distal section 32 facing cover 20 there is formed an elongated blade mounting pad or fitting 33 configured to be received in a suitably configured slot 34 in blade 31. Fitting 33 is standardly configured to detachably be received in blade slot 34 while preventing longitudinal displacement of the substantially planar blade 31 relative to blade carrier 30. The height (or depth) dimension of distal carrier section 32 is smaller than the corresponding dimension of blade 31 so that the cutting edge 35 of the blade is exposed below section 32.

The rearward or proximal end of blade carrier 30 takes the form of a toothed rack 36 having a series of gear teeth extending longitudinally along its bottom edge The teeth of rack 36 are sized and spaced to cooperate with the teeth of pinion 50. Located intermediate the distal section 32 and rack 36 of the blade carrier is an actuator and locking section 60 including an actuator pad 37 projecting upwardly from the top edge of the blade carrier to extend through slot 15 to the housing exterior. Actuator pad 37 is widened at its exposed surface, relative to the top edge of the blade carrier, in order to facilitate finger actuation thereof in the manner described herein. Beneath actuator pad 37 there is a generally elliptical area 38 cut out of the actuator and locking section, the cut out 38 extending entirely through the thickness of blade carrier 30. Cut out 38 is longer along the length dimension of the blade carrier than along the height dimension thereof, and serves to permit the actuator and locking section 60 to be compressed downwardly in response to downward finger pressure applied to the actuator pad 37.

Blade shield 40 is a thin elongated member having a length somewhat shorter than that of blade carrier 30. Shield 40 includes a distal planar shield section 41 and a proximal rack section 42, and is disposed between the blade carrier 30 and cover 20 in the scalpel housing. Shield section 41 includes a longitudinally-extending intermediate section 43 occupying most of its length and terminating in a shield segment 44 at its distal end and a guide segment 45 at its proximal end. Shield segment 44 bends upwardly from longitudinal segment 43 at an angle generally similar to the angle defined by wall section 16 with bottom wall 13 of handle 10. Guide section 45 extends perpendicularly downward from the proximal end of segment 43 so that its bottom edge abuts and rides along the interior surface of bottom wall 23 of cover 20.

Rack 42 is secured to and extends rearwardly from the interior-facing surface of guide segment 45. Gear teeth are defined along the upper edge of rack 42 and are sized and spaced to cooperate with the teeth of pinion 50. In this regard, rack 42 extends along bottom wall 23 of the cover at a location below the pinion 50 so that the teeth on the upper edge of the rack engage the pinion teeth.

Figure 2:
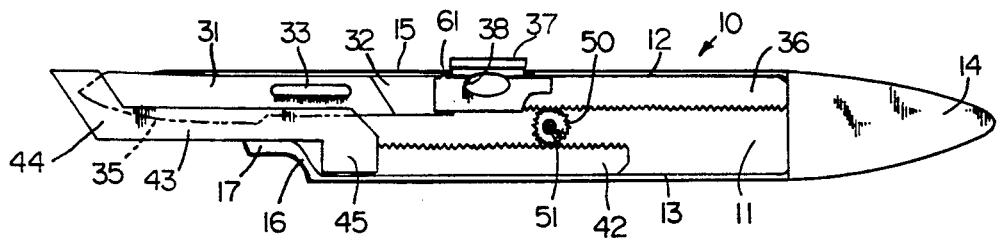
FIG. 2 is a left side view in elevation of the surgical scalpel of FIG. 1 with the cover removed and showing the blade retracted to its protected position
Figure 4:
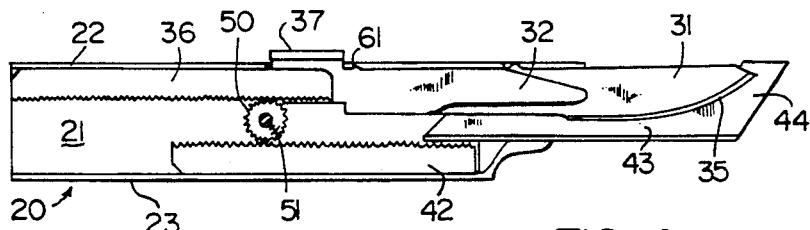
FIG. 4 is a right side view in elevation of the surgical scalpel of FIG. 1 with the handle removed and showing the blade retracted to its protected position.
Figure 5:
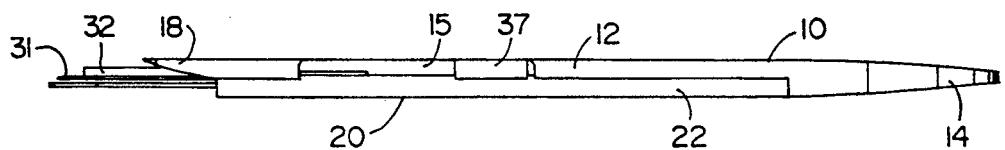
FIG. 5 is a top view in plan of the surgical scalpel of FIG. 1 showing the blade retracted.

The actuator and locking section 60 of blade carrier 30 includes two small stop members projecting upwardly from its upper edge near opposite sides of actuator pad 37. Specifically, a forward stop 61 extends upward from a location just forward of actuator pad 37, and a rearward stop 62 extends upward from a location just rearward of the actuator pad. The stops project from the longitudinal upper edge of blade carrier 30 that normally rides along the interior surface of upper wall 12 of handle 10. The height of the stops is less than the height (or thickness) of wall 12. The interior surface of handle upper wall 12 has longitudinally spaced recesses 63 and 64 defined therein proximate the forward and rearward ends, respectively, of slot 15. As best illustrated in FIG. 6, recess 63 is positioned to receive stop 61 in the forwardmost longitudinal position of blade carrier 30 wherein the cutting edge of blade 31 is exposed. In this position the rearward stop 62 is disposed in slot 15 so that there is no interference between stop 62 and wall 12, and the upper edge of the blade carrier is free to abut wall 12. As best illustrated in FIG. 7, rearward recess 64 is positioned to receive rearward stop 62 in the fully retracted position of blade carrier 30, wherein the blade is protected by shield 40. In this position the forward stop 61 is disposed in slot 15 so as not to force the upper edge of blade carrier 30 away from handle wall 12. In this retracted position, as best illustrated in FIGS. 2, 4 and 5, shield section 41 is disposed immediately adjacent blade 31 with intermediate shield segment 43 extending below and blocking access to the bottom portion of the cutting edge of blade 31, and with forward shield segment 44 disposed adjacent and forward of the forward portion of the cutting blade to thereby block access to the blade cutting edge. In this regard, the specific shapes of the segments of shield section 41 are not critical, other than the fact that they must be selected to block access to the cutting edge of the blade when adjacent the blade in the retracted position of blade carrier 30. Likewise, the configuration of stops 61, 62 and recesses 63, 64 are not critical except as to serve the stop functions and define the extreme positions (i.e., retracted and extended) of the blade carrier.

Figure 3:
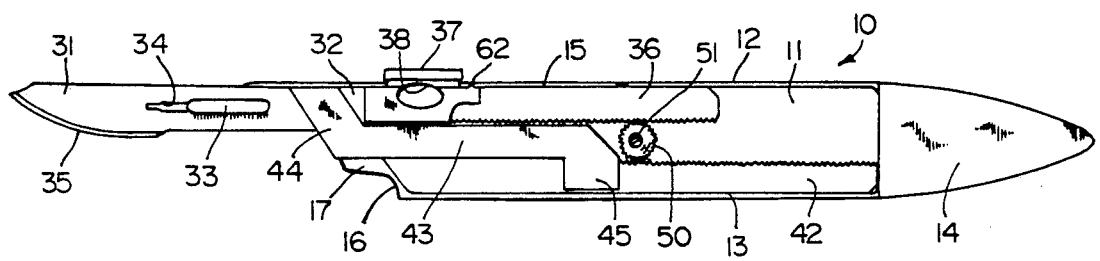
FIG. 3 is a left side view in elevation of the surgical scalpel of FIG. 1 with the cover removed and showing the blade extended to its cutting position.

In operation, it is initially assumed that the blade is in its protected position (i.e., the blade carrier is retracted rearwardly) as best illustrated in FIGS. 2, 4, 5 and 7. Shield segment 43 is disposed immediately adjacent blade 31 and extends below and forwardly of the blade cutting edge to prevent accidental cutting of an individual during handle of the scalpel. The normal position of rearward stop 62 in recess 64 prevents inadvertent longitudinal movement of the blade carrier relative to handle 10. When it is desired to expose the cutting edge of blade 31 during a surgical procedure, it is only necessary to press down on actuator pad 37 (as best illustrated in FIG. 7) and then slide the actuator pad forwardly in slot 15. Once the rearward stop 62 clears recess 64, the downward pressure on actuator pad 37 can be released and the pad need only be pushed in a forward direction until forward stop 61 snaps into forward recess 63, a situation that is tactually sensed by the surgeon's hand. In this position, as best illustrated in FIGS. 3 and 6, the blade carrier is fully extended and the blade is exposed and available for performing cutting operations. When it is desired to retract the cutting blade, actuator pad 37 is once again pressed downward and then slid backward toward the rearward end of slot 15 until rearward stop 62 snaps into rearward recess 64. This occurrence is also tactually sensed by the surgeon's hand.

As the blade carrier is slid in either direction, its rack 36 engages pinion 50 and causes it to rotate. The blade shield rack 42 is driven by the pinion 50 in a longitudinal direction opposite to the direction of motion of the blade carrier. As a consequence, the relative motion between the shield and the blade is twice the longitudinal motion of actuator pad 37.

Figure 8:
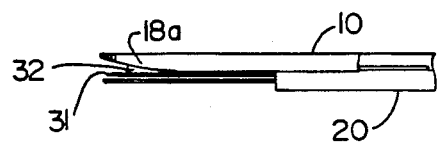
FIG. 8 is a detailed top view in plan of a portion of an alternative embodiment of the surgical scalpel configuration according to the present invention.

In the preferred embodiment illustrated in FIGS. 1–7, the most retracted position of the blade carrier 30 leaves the forward end of blade 31 in a position wherein it extends forwardly of the finger-like distal end projection 18 of handle 10. However, the immediate side-by-side adjacency of the shield and blade preclude accidental cutting of one's hand by the blade cutting edge. In an alternative construction, as illustrated in FIG. 8, the forward projection 18a extends a sufficiently greater distance to block access to blade 31 from the handle side of the housing in the retracted position of the blade.

In the preferred embodiment of the invention, handle 10, cover 20, blade carrier 30, blade shield 40 and pinion 50 are each made of molded plastic material. The plastic material may be of a type that deforms when subjected to temperatures used in sterilizing medical instruments since the scalpel is intended to be disposable, rather than sterilized, after a single use. Preferably, each of these elements is molded as an integral piece, thereby rendering assembly of the scalpel a simple matter of inserting the blade carrier 30 with blade 31 into handle 10, placing pinion 50 on pin 51, disposing blade shield 40 in handle 10 and then securing cover 20 to the handle. The manufacture of parts and the assembly of those parts require relatively little expense, thereby rendering the scalpel sufficiently inexpensive that it may be disposed of after a single use.

The scalpel has a thin profile, typically less than one-quarter inch in width at its widest point, and a height on the order of nine-sixteenths inch. The length of the handle, in the embodiments of FIGS. 1-7, is typically on the order of four and one-half inches. The resulting configuration permits the scalpel to be held easily in the surgeon's hand and positioned such that the thumb and side of the middle finger are disposed on opposite sides of the scalpel and the index finger disposed along the top edge of the scalpel. In this position, the surgeon need only move his or her index finger downwardly and forwardly to extend or retract the cutting blade. Alternatively, if so desired, the surgeon may hold the scalpel between the thumb and index finger and move either of those fingers to the top edge for purposes of displacing the actuator pad.

The double rack arrangement cooperating with pinion 50 permits a relatively small longitudinal movement of the surgeon's actuating finger to effect twice the movement of the cutting blade relative to the shield. The overall result is a disposable scalpel structure that is easily held and manipulated by the surgeon, easily shipped and stored without danger of damage, and wherein the actuating mechanism for exposing and retracting the blade is readily actuated and ultimately accessible.

Having described a preferred embodiment of a new and improved surgical scalpel constructed in accordance with the present invention, it is believed that other modifications, variations and changes will be suggested to persons skilled in the art in view of the teachings set forth herein. It is therefore to be understood that all such variations, modifications and changes are believed to fall within the scope of the present invention as defined by the appended claims.

What is claimed is:

1. A surgical scalpel comprising:
   an elongated housing having proximal and distal ends;
   a substantially planar surgical blade disposed at the distal end of said housing, said blade having a cutting edge extending generally along the length of the housing;
   actuating means secured in said housing and extending outwardly therefrom, said actuating means disposed in a position to be engaged by a finger of a user when holding said housing in a position of normal use and mounted for movement generally longitudinally of said housing;
   a blade shield disposed in said housing and constructed to cover at least said cutting edge, said blade shield mounted for movement between a blade-guarded position in which said cutting edge is protected and a blade-exposed position in which said blade may be used for cutting;
   linkage means disposed in said housing for coupling the movement of said actuating means to said blade shield relative to said blade so as to move said blade shield between the bladeguarded and blade-exposed positions, said linkage means including means for causing the distance of movement of said blade shield relative to said blade to be substantially greater than the distance of movement of said actuating means; and
   a blade carrier for supporting said cutting blade and disposed in said housing for longitudinal movement between an extended position wherein said cutting edge of said blade projects forwardly of said housing for use in a cutting procedure, and a retracted position wherein said cutting edge of said blade is at least partially retracted into said housing;
   wherein said actuating means comprises an actuable member fixedly secured to one of said blade carrier and blade shield for longitudinal movement therewith relative to said housing;
   wherein said linkage means comprises means cooperatively engaged with both said blade carrier and said blade shield for moving said blade carrier and blade shield in opposite longitudinal directions in response to longitudinal movement of said actuable member; and
   wherein said blade-guarded position of said blade shield corresponds to said retracted position of said blade carrier, and wherein said blade-exposed position of said blade shield corresponds to said extended position of said blade carrier.

2. A surgical scalpel as recited in claim 1 wherein said housing has an upper wall facing oppositely from said cutting edge, and wherein said actuable member projects upwardly through said upper wall and is movable longitudinally along said upper wall.

3. A surgical scalpel as recited in claim 2 wherein said means cooperatively engaged with said blade carrier and said blade shield comprises:
   a toothed pinion disposed in said housing for rotation about an axis oriented perpendicular to said length of said housing;
   a first toothed rack secured to said blade carrier for longitudinal movement therewith and disposed in cooperative engagement with said pinion;
   a second toothed rack secured to said blade shield for longitudinal movement therewith and disposed in cooperative engagement with said pinion;
   wherein said first and second racks engage said pinion at respective diametrically opposed locations; and
   whereby longitudinal movement of said actuable member directly moves said one of said blade carrier and blade shield to rotate said pinion and thereby longitudinally move the other of said blade carrier and blade shield.

4. A surgical scalpel as recited in claim 3 wherein said first and second racks are disposed entirely within said housing.

5. A surgical scalpel as recited in claim 3 further comprising stop means for defining said extended and retracted positions of said blade carrier and for minimizing inadvertent movement of said blade carrier from said extended and retracted positions.

6. A surgical scalpel as recited in claim 5 wherein said stop means comprises first and second upwardly extending and longitudinally spaced stops secured to said one of said blade carrier and blade shield, an first and second recesses defined in the interior surface of said upper wall to receive said first and second stops, respectively, in said extended and retracted positions, respectively, of said blade.

7. A surgical scalpel as recited in claim 6 wherein said actuable member includes resilient means responsive to downward pressure applied thereto for displacing said stops from said recesses to permit longitudinal movement of said actuable member relative to said housing.

8. A scalpel comprising:
an elongated handle;
an elongated cover fixedly secured to said handle to define a housing between said cover and said handle, said housing having an open distal end an upper wall with a longitudinal slot defined therein;
an elongated blade carrier disposed in said housing for longitudinal movement relative to said housing;
a cutting blade removably secured to said blade carrier for longitudinal movement therewith and having a cutting edge extending along its bottom;
an elongated blade shield disposed in said housing for longitudinal movement relative to said housing and to said blade carrier;
an actuator fixedly secured to one of said blade carrier and said blade shield and extending out from said housing via said slot, said actuator being movable longitudinally of said housing along said slot between first and second positions; and
linkage means responsive to longitudinal movement of said actuator and said one of said blade carrier and blade shield for moving the other of said blade carrier and blade shield longitudinally of said housing in a direction opposite the direction of movement of said actuator;
wherein in said first position of said actuator said blade shield protects said cutting edge against inadvertent contact with an external body, and in said second position of said actuator said cutting edge is exposed for use in a surgical procedure.

9. A scalpel as recited in claim 8 wherein said blade shield includes a substantially planar distal segment disposed immediately adjacent said blade in said first position of said actuator, said distal segment being sufficiently large in area to cover and prevent access to the entirety of said cutting edge.

10. A scalpel as recited in claim 8 further comprising:
engagable stop means for preventing, when engaged, inadvertent longitudinal movement of said actuator from said first and second positions; and
means responsive to downward pressure applied to said actuator for disengaging said stop means.

11. A scalpel as recited in claim 8 wherein said linkage means comprises:
a toothed pinion disposed in said housing for rotation about an axis oriented perpendicular to the length of said housing;
a first toothed rack secured to said blade carrier for longitudinal movement therewith and disposed in cooperative engagement with said pinion;
a second toothed rack secured to said blade shield for longitudinal movement therewith and disposed in cooperative engagement with said pinion; and
wherein said first and second racks engage said pinion at respective diametrically opposed locations;
whereby longitudinal movement of said actuator directly moves said one of said blade carrier and said blade shield to cause rotation of said pinion and thereby longitudinally displace said other of said blade carrier and blade shield.

12. A method for automatically guarding and exposing the substantially planar blade of a surgical scalpel having an elongated housing and a direction of cut extending along the length of the housing, said method comprising the steps of:
(a) providing a blade shield adjacent said blade, mounted so as to be moved between blade-guarded and blade-exposed positions;
(b) positioning an actuating member on said scalpel so as to be moved longitudinally and generally parallel to both the plane of the blade and the direction of cut by a finger of a user when the scalpel is grasped for normal use; and
(c) coupling the actuator member movement to said blade shield so that the blade shield is moved over a substantially greater distance than said actuating member;
wherein stop (c) comprises simultaneously moving said blade and said blade shield in opposite longitudinal directions in response to longitudinal movement of said actuator.

13. A method as recited in claim 12 further comprising the stop of discarding said scalpel after a single surgical procedure.

* * * * *